US009331265B2

(12) United States Patent
Chakrabartty

(10) Patent No.: US 9,331,265 B2
(45) Date of Patent: May 3, 2016

(54) NON-VOLATILE MEMORY WITH LINEAR HOT-ELECTRON INJECTION TECHNIQUE AND STRAIN GAUGE USING THE SAME

(71) Applicant: Board of Trustees of Michigan State University, East Lansing, MI (US)

(72) Inventor: Shantanu Chakrabartty, Williamston, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 14/380,122

(22) PCT Filed: Jan. 28, 2013

(86) PCT No.: PCT/US2013/023407
§ 371 (c)(1),
(2) Date: Aug. 21, 2014

(87) PCT Pub. No.: WO2013/126181
PCT Pub. Date: Aug. 29, 2013

(65) Prior Publication Data
US 2015/0027237 A1 Jan. 29, 2015

Related U.S. Application Data

(60) Provisional application No. 61/602,247, filed on Feb. 23, 2012.

(51) Int. Cl.
| | |
|---|---|
| *G01L 1/16* | (2006.01) |
| *H01L 41/113* | (2006.01) |
| *G11C 16/34* | (2006.01) |
| *G11C 27/00* | (2006.01) |
| *G01B 7/16* | (2006.01) |
| *A61B 5/00* | (2006.01) |

(Continued)

(52) U.S. Cl.
CPC .......... *H01L 41/1132* (2013.01); *A61B 5/4509* (2013.01); *A61B 5/4519* (2013.01); *A61B 5/4533* (2013.01); *A61B 5/6847* (2013.01); *G01B 7/18* (2013.01); *G11C 16/3468* (2013.01); *G11C 16/3481* (2013.01); *G11C 16/3486* (2013.01); *G11C 27/005* (2013.01); *H01L 27/20* (2013.01); *H01L 29/7884* (2013.01)

(58) Field of Classification Search
CPC .................. G01N 2203/0623; G11C 16/3468; H01L 41/1132
USPC ............................... 73/862.68, 780, 760, 777
See application file for complete search history.

(56) References Cited

U.S. PATENT DOCUMENTS

| | | |
|---|---|---|
| 4,769,797 A | 9/1988 | Murakami |
| 4,797,856 A | 1/1989 | Lee et al. |

(Continued)

*Primary Examiner* — Max Noori
(74) *Attorney, Agent, or Firm* — Harness, Dickey & Pierce, P.L.C.

(57) ABSTRACT

A linear hot-electron injection technique is provided for a non-volatile memory arrangement. The non-volatile memory is comprised of: a floating gate transistor; a capacitor with a first terminal electrically coupled to the gate node of the floating gate transistor; a current reference circuit electrically coupled to the source node of the floating gate transistor; and a feedback circuit electrically coupled between the source node of the floating gate transistor and a second terminal of the capacitor. The feedback circuit operates to adjust a voltage at the gate node of the floating gate transistor in accordance with a source-to-drain voltage across the floating gate transistor.

18 Claims, 13 Drawing Sheets

(51) Int. Cl.
*H01L 27/20* (2006.01)
*H01L 29/788* (2006.01)

(56) References Cited

U.S. PATENT DOCUMENTS

| | | |
|---|---|---|
| 5,200,919 A | 4/1993 | Kaya |
| 5,386,132 A | 1/1995 | Wong |
| 5,880,993 A | 3/1999 | Kramer et al. |
| 6,040,996 A | 3/2000 | Kong |
| 7,388,247 B1 * | 6/2008 | Lagnado ............... H01G 5/019 257/312 |
| 8,711,599 B2 * | 4/2014 | Schubert ............... G11C 11/22 365/145 |
| 2002/0111756 A1 | 8/2002 | Modgil |
| 2008/0047355 A1 | 2/2008 | Chakrabartty et al. |
| 2009/0120200 A1 * | 5/2009 | Chakrabartty .......... A61F 2/468 73/808 |

* cited by examiner

US 9,331,265 B2

NON-VOLATILE MEMORY WITH LINEAR HOT-ELECTRON INJECTION TECHNIQUE AND STRAIN GAUGE USING THE SAME

CROSS-REFERENCE TO RELATED APPLICATIONS

This application is a U.S. National Phase Application under 35 U.S.C. 371 of International Application No. PCT/US2013/023407 filed on Jan. 28, 2013 and published as WO 2013/126181 on Aug. 29, 2013. This application claims the benefit of U.S. Provisional Application No. 61/602,247, filed on Feb. 23, 2012. The entire disclosures of the above applications are incorporated herein by reference.

GOVERNMENT RIGHTS

This invention was made with Government support under Contract No. 0954752 and Contract No. 1127606 awarded by the National Science Foundation. The U.S. Government has certain rights in this invention.

FIELD

The present disclosure relates to a linear hot-electron injection technique which simplifies the programming procedure for a non-volatile memory as well as a self-powered strain gauge enabled by this technique.

BACKGROUND

As non-volatile programmable circuit elements, floating-gate (FG) transistors have been extensively used for designing EEPROMs and flash memories, for designing analog signal processors, and for designing energy scavenging sensors. In particular, when a large number of on-chip voltage and current biases are required, as is the case for analog neural-network ICs and field-programmable analog arrays (FPAAS), floating-gates provide an ultra-compact approach for implementing field-programmable biases. Also, due to the non-volatile nature of the FG transistors, the bias values are retained across brown-outs and power-outages, making the technology also attractive for energy scavenging sensors.

The common method for programming FG transistors is by using Fowler-Nordheim (FN) tunneling or by using hot-electron injection. The procedure is illustrated in FIGS. 1A and 1B which shows the cross-sectional area of an FG p-channel MOS (pMOS) transistor and its layout. The polysilicon gate of the pMOS transistor is electrically insulated by silicon-dioxide (hence the name "floating-gate"), and any electron injected onto the gate is retained for a long period of time (8 bits precision for 8 years). FN tunneling removes the electrons from FG node by applying a high-voltage V_tun (>15V in 0.5 μm CMOS process) across a parasitic nMOS capacitor C_tun. However, the use of high-voltage also restricts the usage of FN tunneling for selective programming and therefore it is only employed to globally remove the electrons from all on-chip floating-gates.

Hot-electron injection, however, requires lower voltage (≈4.2V in 0.5 μm CMOS process) than tunneling and hence is the primary mechanism for selective programming of floating-gates. The hot-electron programming procedure, as shown in FIG. 1A, involves selection of the FG transistor (using switches) followed by applying V_sd>4.2V across the source and the drain terminals. The large electric field near the drain of the pMOS transistor creates impact-ionized hot-electrons whose energy when exceeds the gate-oxide potential barrier (≈3.2 eV) can get injected onto the floating-gate. Because the hot-electron injection in a pMOS transistor is a positive feedback process and can only be used to add electrons to the floating-gate, the process needs to be carefully controlled and periodically monitored to ensure the floating-gate voltage is programmed to a desired precision. The methods proposed in literature achieve the desired precision either by adjusting the duration for which the FG transistor is injected or by adjusting the magnitude of the injection pulses.

In this disclosure, a linear hot-electron injection technique is set forth which simplifies the programming procedure and can achieve a linear programming range as large as 4V. The procedure employs an active feedback mechanism to ensure that all the non-linear factors affecting the hot-electron injection are held constant, thus achieving a linear, stable and controllable injection rate. This is unlike the feedback methods that have been previously used for programming FG memories, where an off-chip amplifier circuit is used for indirect programming. The proposed linear injection technique results in a much simpler and more predictable programming procedure.

Additionally, the proposed linear injection technique is then used to develop a self-powered static-strain sensor.

This section provides background information related to the present disclosure which is not necessarily prior art.

SUMMARY

A linear hot-electron injection technique is provided for a non-volatile memory arrangement. The non-volatile memory is comprised of: a floating gate transistor; a capacitor with a first terminal electrically coupled to the gate node of the floating gate transistor; a current reference circuit electrically coupled to the source node of the floating gate transistor; and a feedback circuit electrically coupled between the source node of the floating gate transistor and a second terminal of the capacitor. The feedback circuit operates to adjust a voltage at the gate node of the floating gate transistor in accordance with a source-to-drain voltage across the floating gate transistor, thereby achieving a linear injection technique. The non-volatile memory further includes a switch electrically coupled between the second terminal of the capacitor and ground, such that the switch is opened to inject current into the floating gate transistor and is closed to remove electrons from the floating gate transistor.

In one aspect of the disclosure, the feedback circuit is further defined as an operational amplifier having an inverting terminal electrically coupled to the source node of the floating gate transistor, a non-inverting terminal electrically coupled to a reference voltage and an output electrically coupled to the second terminal of the capacitor.

In another aspect of the disclosure, a self-powered static-strain sensor is implemented using the linear hot-electron injection technique. The sensor is self-powered by piezoelectric transducers which convert mechanical energy due to strain-variations into electrical energy. A differential injector topology is used to measure static-strain by integrating the difference between the signal energy generated during positive and negative strain-cycles. Each differential integrator is implemented using the non-volatile memory arrangement noted above.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

DRAWINGS

Figure 1A:
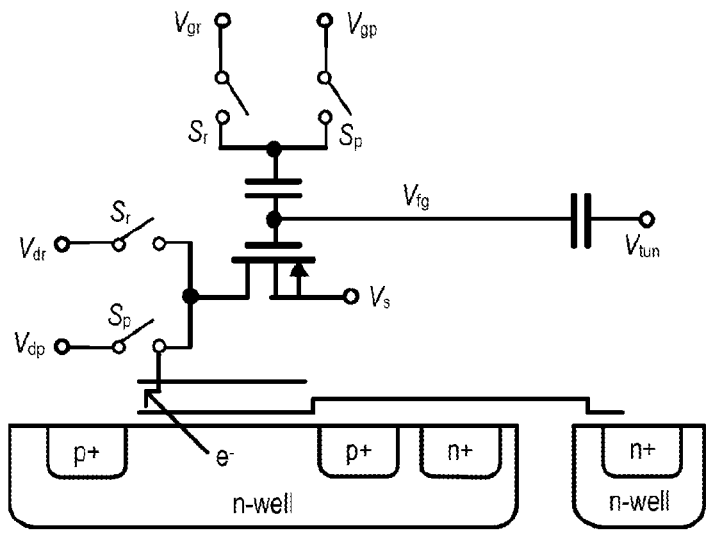
FIG. 1A is a cross-sectional view of a pMOS FG transistor along with the circuits used for conventional hot-electron programming.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Figure 2A:
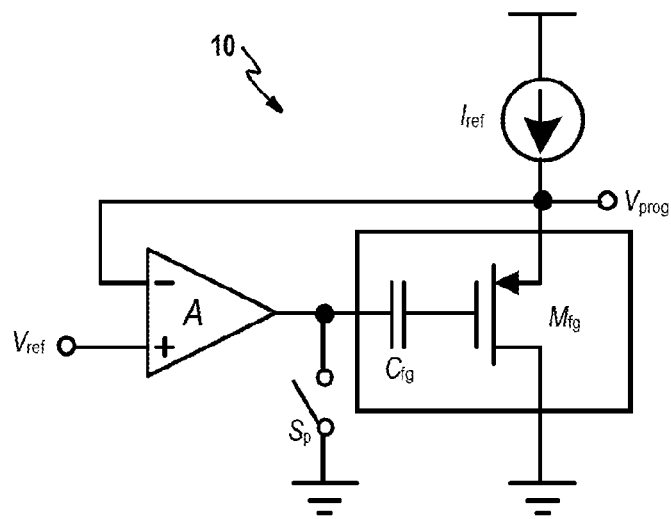
FIG. 2A is a schematic of an exemplary circuit arrangement for a non-volatile memory that employs a linear hot-electron injection technique.

FIG. 2A depicts an exemplary circuit arrangement 10 for a non-volatile memory that employs a linear hot-electron injection technique. The circuit arrangement 10 is comprised of a floating gate transistor $M_{fg}$, a capacitor $C_{fg}$, a current reference source $I_{ref}$ and a feedback circuit. The feedback circuit is electrically coupled between a source node of the floating gate transistor $M_{fg}$ and a terminal of the capacitor $C_{fg}$ while the other terminal of the capacitor $C_{fg}$ is electrically coupled to a gate node of the floating gate transistor $M_{fg}$. More specifically, the feedback circuit may be implemented by an operational amplifier A having an inverting terminal electrical coupled to the source node of the floating gate transistor $M_{fg}$, a non-inverting terminal electrically coupled to a reference voltage and an output electrically coupled to the second terminal of the capacitor. The circuit arrangement further includes a switch $S_p$ electrically coupled between the second terminal of the capacitor and ground and a controller (not shown) interfaced with the switch $S_p$ to control operation thereof. Other arrangements for the circuit are also contemplated by this disclosure.

Operating principle for the linear hot-electron injection technique is set forth in detail below. Impact-ionized hot-electron injection (IHEI) current, $I_{inj}$, in a pMOS transistor has been shown to be dependent on the transistor source current $I_s$, the source-to-drain voltage $V_{sd}$ and the gate-to-drain voltage $V_{gd}$ across the transistor. This dependence can be expressed in functional form as $$I_{inj} = f(I_s, V_{sd}, V_{gd}), \quad (1)$$

where $f(\cdot)$ is an arbitrary function. To our knowledge, the exact form of the mathematical function $f(\cdot)$ is not known and in literature many empirical models have been proposed to approximate $f(\cdot)$. For example, the following IHEI model has been shown to be valid for all operating regions of the transistor (weak, moderate and strong inversion):

$$I_{inj} = \alpha I_s \exp\left(\frac{\lambda V_{sd}}{V_{inj}}\right) \exp\left[-\frac{\beta}{(V_{gd}+\delta)^2}\right], \quad (2)$$

where $\alpha$, $\lambda$, $\beta$, $\delta$ and $V_{inj}$ are the parameters of the model which are estimated from measured data. For the proposed linear injection technique, all the factors which affect the injection current such as $I_s$, $V_{sd}$ and $V_{gd}$ are held constant so that the injection current $I_{inj}$ according to equation (1) is constant. Continuing with circuit arrangement 10, its operational principle is explained with reference to FIGS. 2B and 2C.

Figure 2B:
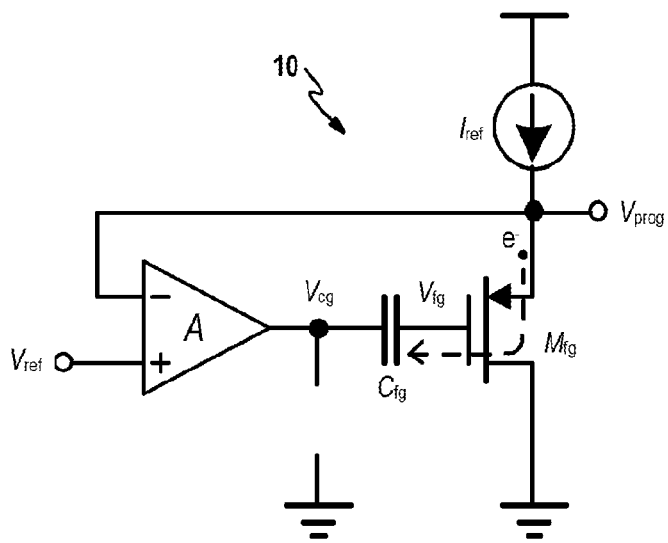
FIGS. 2B and 2C are schematics illustrating the non-volatile memory during programming mode and biasing mode, respectively.
Figure 2C:
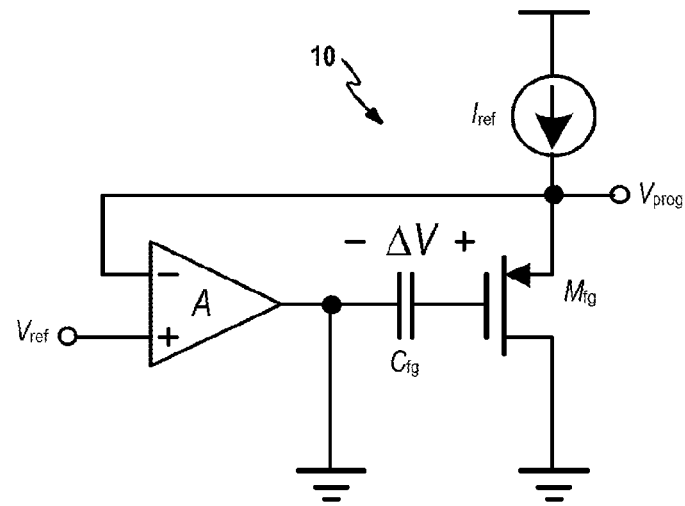

During the programming or injection mode of circuit in FIG. 2B, the switch $S_p$ is open which activates the negative feedback loop formed by the opamp A and the floating-gate transistor $M_{fg}$. The source current is held constant at $I_{ref}$ which ensures that the source-to-gate voltage $V_{sd}$ is held constant by appropriately adjusting the control-gate voltage $V_{cg}$. Thus, according to equation (1) the injection current will remain constant. The programming is enabled for a fixed duration $t_p$ which ensures that a fixed amount of charge is injected onto the floating-gate. During the read-out mode as shown in FIG. 2C, the switch $S_p$ is closed which connects the control-gate to a reference potential (ground in this case). The floating-gate voltage $V_{fg}$ of the pMOS transistor is determined by the charge injected during the programming phase and the capacitor $C_{fg}$. The formal analysis of the linear injector is now presented by taking into account the effect of the finite gain of the opamp and injection small signal parameters derived from the measurement results.

According to equation (1), the injection current $I_{inj}$ in the circuit arrangement 10 of FIG. 2B (without considering the effect of thermal-noise) is given by $$I_{inj} = f(I_{ref}, V_s, V_{fg}), \quad (3)$$

which can be linearized about the injection current $I_{inj}^0$ for incremental source voltage $\Delta V_{fg}$ as $$I_{inj} = I_{inj}^0 + G_s \Delta V_s + G_{fg} \Delta V_{fg}, \quad (4)$$

where $G_s=\partial I_{inj}/\partial V_s$ denotes the injection transconductance parameter with respect to the source terminal and $G_{fg}=\partial I_{inj}/\partial V_{fg}$ denotes the injection transconductance parameter with respect to the floating-gate terminal. Assuming the reference current is constant, the small-signal analysis of the pMOS current leads to $$\Delta I_{ref}=(g_m+g_d)\Delta V_s-g_m\Delta V_{fg}=0, \quad (5)$$

where $g_m=\partial I_{ref}/\partial V_g$ and $g_d=\partial I_{ref}/\partial V_d$ are the transconductance small-signal parameters with respect to the gate and drain terminals. Then $\Delta V_s \approx \Delta V_{fg}$ when $g_m \gg g_d$ for the pMOS transistor in saturation region. If $V_{tun}$, $V_s$, $V_d$ and $V_b$ denote the tunneling voltage, source voltage, drain voltage and bulk voltage of the floating-gate transistor, and $C_{fg}$, $C_{tun}$, $C_s$, $C_d$, $C_b$ denote the capacitances (parasitic and non-parasitic) which couple these nodes with the floating-gate, then the charge stored on the floating-gate can be expressed as $$Q=C_{fg}(V_{fg}-V_{cg})+C_{tun}(V_{fg}-V_{tun})+C_s(V_{fg}-V_s)+C_d(V_{fg}-V_d)+C_b(V_{fg}-V_b). \quad (6)$$

Since the feedback topology in the circuit of FIG. 2B maintains all the node voltages except $V_{fg}$ at a constant potential, the charge variation $\Delta Q$ can be simplified as $$\Delta Q=\Delta V_{fg}C_T \quad (7)$$

where $C_T=(C_{fg}C_{tun}+C_s+C_d+C_b)$ is the total capacitance associated with the floating-gate. If the gain of the opamp is assumed to be $A_v$, then the feedback loop ensures $$\Delta V_{cg}+\frac{\Delta Q}{C_T}=-A_v\Delta V_s+\frac{\Delta Q}{C_T}=\Delta V_{fg}\approx\Delta V_s, \quad (8)$$

Thus, $$\Delta V_s=\frac{\Delta Q}{C_T(1+A_v)}, \quad (9)$$

where, $V_s$ remains constant for infinite $A_v$. The charge variation $\Delta Q$ in (9) can be expressed with the injection current as $$\Delta Q=-I_{inj}\Delta t. \quad (10)$$

Applying equations (8)-(10) into (4) and letting $\Delta t \to 0$, the following first-order differential equation is obtained:

$$\frac{dI_{inj}}{dt}+\frac{G_s+G_{fg}}{C_T(1+A_v)}I_{inj}=0, \quad (11)$$

which leads to $$I_{inj}=I_{inj}^0\exp\left[-\frac{(G_s+G_{fg})t}{C_T(1+A_v)}\right]. \quad (12)$$

Equation (12) shows that the finite gain of the opamp will introduce temporal dependency in the injection current which will introduce an error in programming of the floating-gate voltage. Given the duration of the injection pulse to be $t_p$, the programming error can be computed as $$\frac{\Delta V_{fg}}{V_{fg}}=\frac{\Delta I_{inj}}{I_{inj}}=\exp\left[-\frac{(G_s+G_{fg})t_p}{C_T(1+A_v)}\right]. \quad (13)$$

Figure 3:
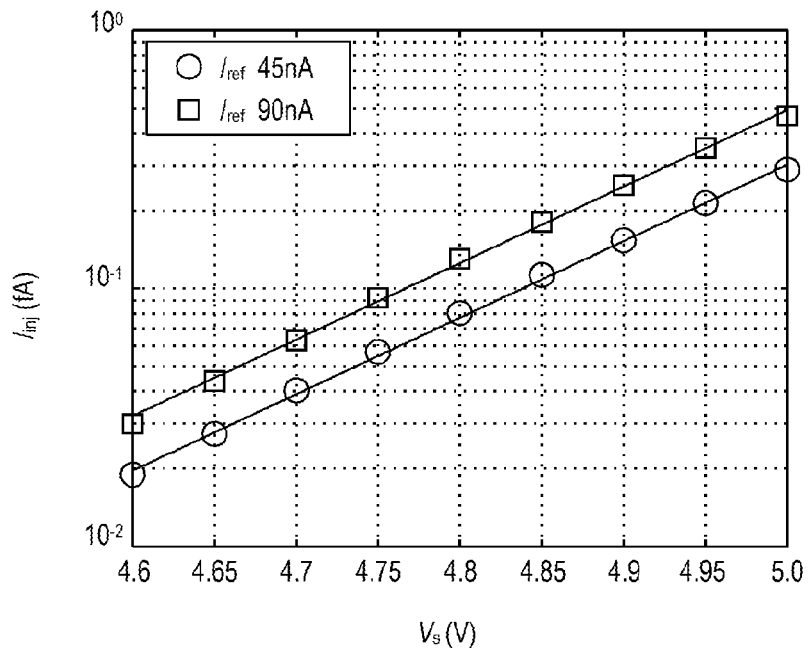
FIG. 3 is a graph showing the measured injection current into the memory circuit when the source voltage is varied.

FIG. 3 shows the measured injection current when the source voltage is varied and all the other parameters are held constant. Based on the measured data, the small signal parameter $G_s$, $G_{fg}$ can be estimated to range from 0.149 fS to 2.316 fS when the reference current is changed between 45 nA and 90 nA. Hence, based on equation (13), an amplifier with a small-signal gain of 40 dB should be enough to achieve a linear injection resolution greater than 16-bit. However, the programming accuracy will also be affected by the thermal noise while injection electrons onto the floating-gate capacitor. This error is approximately given by $V_n \approx \sqrt{KT/C_T}$, where $C_T$ is the total capacitance (including parasitics) at the floating-gate. For our implementation $C_T \approx 100$ fF which leads to $V_n \approx 200$ μV. Measurements that show that thermal noise is indeed the limiting factor determining the accuracy of the proposed linear programming technique.

Figure 1B:
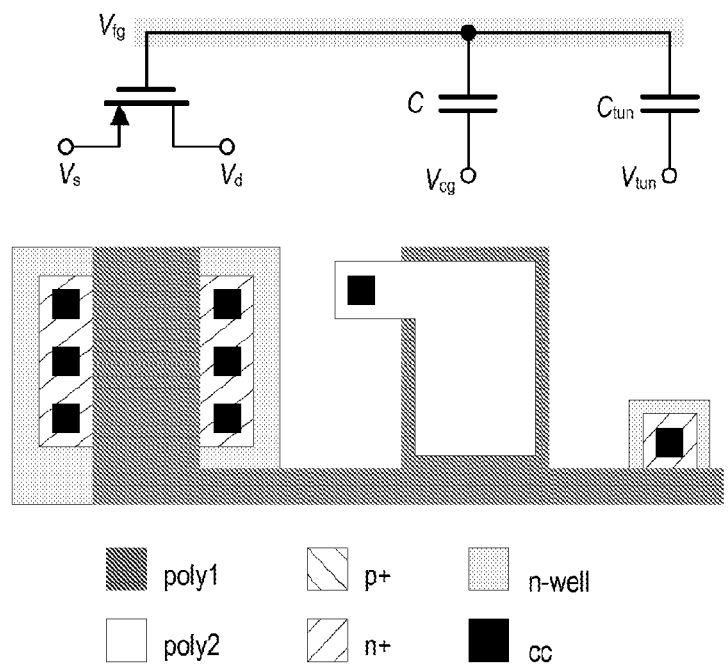
FIG. 1B is a diagram depicting an exemplary layout of the pMOS FG transistor.
Figure 4:
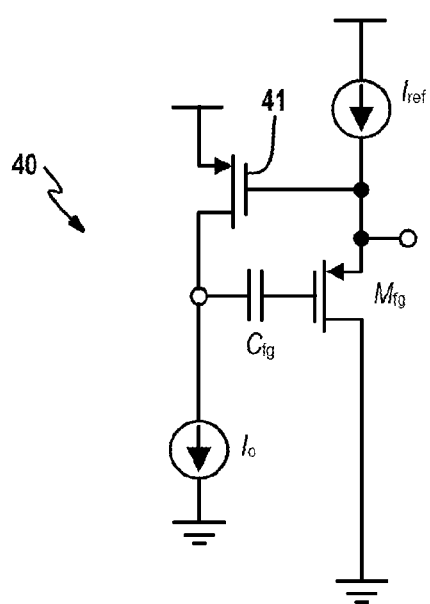
FIG. 4 is a schematic of an alternative circuit arrangement for the non-volatile memory using a single-stage, single-ended amplifier.

FIG. 4 depicts an alternative embodiment of a non-volatile memory 40 that employs a linear hot-electron injection technique. In this arrangement, the feedback circuit is implemented using a single stage, single-ended amplifier 41 (in place of the differential amplifier shown in FIG. 1). The gate of the feedback pMOS transistor 41 is connected to the source of the floating-gate transistor $M_{fg}$ and forms a common-source amplifier biased using the current sink $I_0$; otherwise, the memory circuit operates in the manner described above. This configuration also ensures that the source, gate and drain terminals of $M_{fg}$ are held at a constant potential during hot-electron injection. Other implementations for the feedback circuit are also contemplated by this disclosure.

Figure 5:
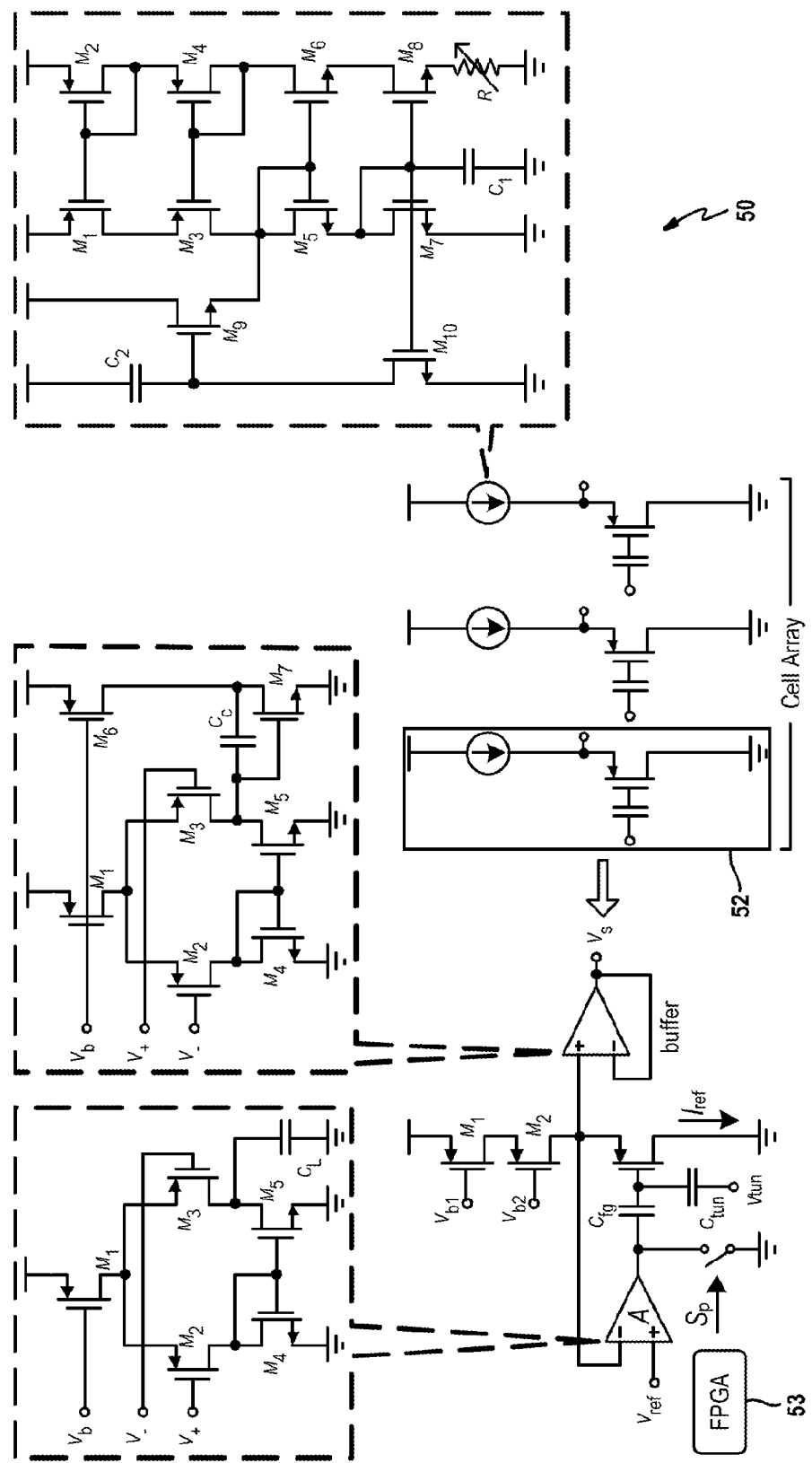
FIG. 5 is a schematic showing an array of memory circuit that employ a linear hot-electron injection technique.

FIG. 5 depicts another non-volatile memory arrangement 50 having an array of memory circuits. Each memory circuit 52 is comprised of a floating gate transistor, a current reference source, a gate capacitor, a tunneling capacitor, a switch and a feedback circuit arranged in the manner described above. Each memory circuit 52 may use an operational amplifier to implement the feedback circuit. Alternatively, a single operational amplifier may be shared amongst the memory circuits 52. A controller 53 is interfaced with the switch in each of the memory circuits for controlling state thereof. In an exemplary embodiment, the controller may be implemented as a field programmable gate array (FPGA).

The circuit shown in FIG. 5 has been prototyped in a 0.5-μm standard CMOS process. For this process the typical gate-oxide thickness is approximately 14 nm and the minimum drain-to-source voltage required to trigger hot-electron injection is 4.2V. For each cell, the constant current reference is implemented using two cascaded pMOS transistors $M_1$ and $M_2$. The source voltage V, of the floating-gate transistor $M_{fg}$ is given by $$V_s=V_{dd}-nV_{bl}+n\frac{\Delta Q}{C_T}, \quad (14)$$

where n is the sub-threshold slope factor, $V_{dd}$ and $V_{bl}$ is the supply and biasing voltages, $\Delta Q$ is the programmed charge and $C_T$ is total capacitance on floating-gate node. The gain requirements on the feedback amplifier is less than 40 dB, which can be achieved using a single stage differential amplifier as shown in FIG. 5. The programmable voltage $\Delta V$ in FIG. 2B is measured using a buffer at $V_s$. The digital pulses controlling the switch $S_p$ are generated using an FPGA where during each programming cycle, $S_p$ is disabled for 50 MS and is enabled during the measurement cycle. In FIG. 5, $C_{tun}$ is a tunneling capacitor which is used for removing electrons from the floating-gate by FN tunneling. A tunable current reference has been used for generating $I_{ref}$ on-chip which reduces the effect of external noise on the measured results. The magnitude of $I_{ref}$ can be varied by tuning the magnitude of an external resistor. The current reference also provides the biasing voltage for the amplifiers A (OP) and the buffer. The FG cell itself with opamp occupies only 60 µm×60 µm area. Table I below summarizes the specification of the fabricated programmable voltage bias generator which has been validated using experiments described in the following sections.

TABLE I

Specifications of the Linear Injection Circuit

| | |
|---|---|
| Process | 0.5-µm standard CMOS |
| Floating-gate capacitance | 100 fF |
| Programming range | 0.1-4.1 V |
| Pulse-width | 50 ms |
| Maximum accuracy | 13.4-bit |
| Minimum injection rate | 6.9 µV/cycle |
| Power dissipation (Programming mode) | 500 nW |
| Power dissipation (Biasing mode) | 250 nW |

The first set of experiments was designed to measure the linear programming range for the proposed voltage bias generator. Before the injection pulses are applied for programming, the supply voltage was ramped up to 6.5V, $S_p$ was enabled and $V_s$ was set to a voltage greater than 4.3V using FN tunneling. The rate of injection was controlled digitally by $S_p$ and by using different combinations of $V_{ref}$ and $I_{ref}$. After each programming cycle, $V_s$ was measured using an off-chip analog-to-digital converter. Since the least significant bit (LSB) voltage for differential non-linearity (DNL) is less than 0.4 mV, the equivalent resolution is above 13.4-bit. The response verifies the hypothesis set forth above that constant injection rate can be obtained by regulating the non-linear parameters of the pMOS transistor. The deviation from the linear injection model occurs at the end points of the operating voltage is due to the finite operating range of the amplifier A. Thus, the proposed approach can achieve a rail-to-rail linear programming range which is an order of magnitude larger than any previous reported results, as shown in the comparison Table II below.

TABLE II

Performance Comparison

| Reference | Range | Accuracy | Integration level | Array programming |
|---|---|---|---|---|
| This work | 4 V | 13.4-bit | Fully on-chip | Enabled |
| [10] | 0.13 V (10-640 pA) | <8-bit | Off-chip | Enabled |
| [11] | 0.3 V (500p-1 µA) | 9-bit | Only I-V | Enabled on-chip |
| [12] | 0.63 V (6p-20 µA) | 9.5-bit | Fully | Enabled on-chip |
| [15] | 1 V | 6.5-bit | Fully | No on-chip |
| [16] | 2 V | 10-bit | Off-chip | No |

Figure 6A:
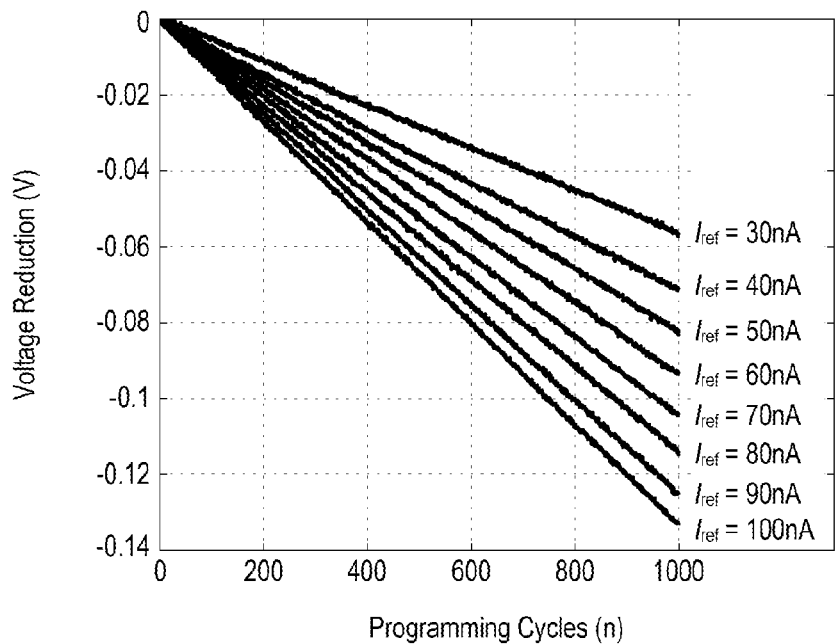
FIGS. 6A and 6B are graphs showing the measured linear injection response when $I_{ref}$ and $V_{ref}$, respectively, is varied.

Based on the injection model expressed by equation (2), the injection current, also known as the injection rate for the linear case, is determined by either $V_{ref}$ or $I_{ref}$. The next set of experiments investigated the effect of changing $V_{ref}$ and $I_{ref}$ on the linear injection rate. For the first experiment, $V_{ref}$ was held constant and different $I_{ref}$ were used. FIG. 6A shows the measured result when $V_{ref}$=4.9V and $I_{ref}$ was varied from 100 nA to 30 nA in steps of 10 nA. For each biasing current, 1,000 programming cycles were applied to the FG element and the voltage reduction after each cycle was recorded. As shown in FIG. 6A, all the programming response are linear and the injection rate decreases monotonically with the reduction in $I_{ref}$, which conforms to the previously reported results for IHEI observed in pMOS transistors.

Figure 6B:
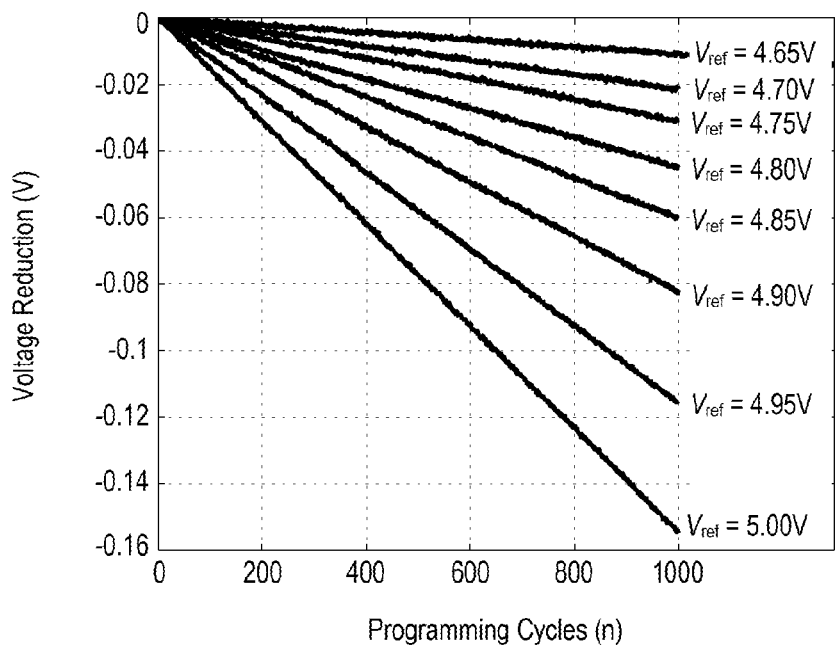

For the next experiment, $I_{ref}$ was held constant and different $V_{ref}$ were used during the injection process. FIG. 6B shows the measured results for the case when $I_{ref}$=50 nA and $V_{ref}$ was varied from 5V to 4.65V in the step of 50 mV. Again, the programming response is linear and the injection rate decreases monotonically with the reduction in $V_{ref}$.

For both the experiments, the average injection rate can be calculated using linear regression over the measured data. It can be readily shown that a slower injection rate, or a finer resolution, can be achieved with smaller $V_{ref}$ or $I_{ref}$, however, at the cost of longer programming time. From the experiments, the smallest injection rate was found to be 6.9 µV/cycle when $V_{ref}$=4.6V and $I_{ref}$=30 nA. The largest linear injection rate than can be achieved using the circuit in FIG. 4 is 250 µV/cycle when $V_{ref}$=5V and $I_{ref}$=100 nA. Also note that increasing capacitor $C_{fg}$ in FIG. 4 should increase the programming accuracy, but at the expense of reduced programming speed.

Figure 7:
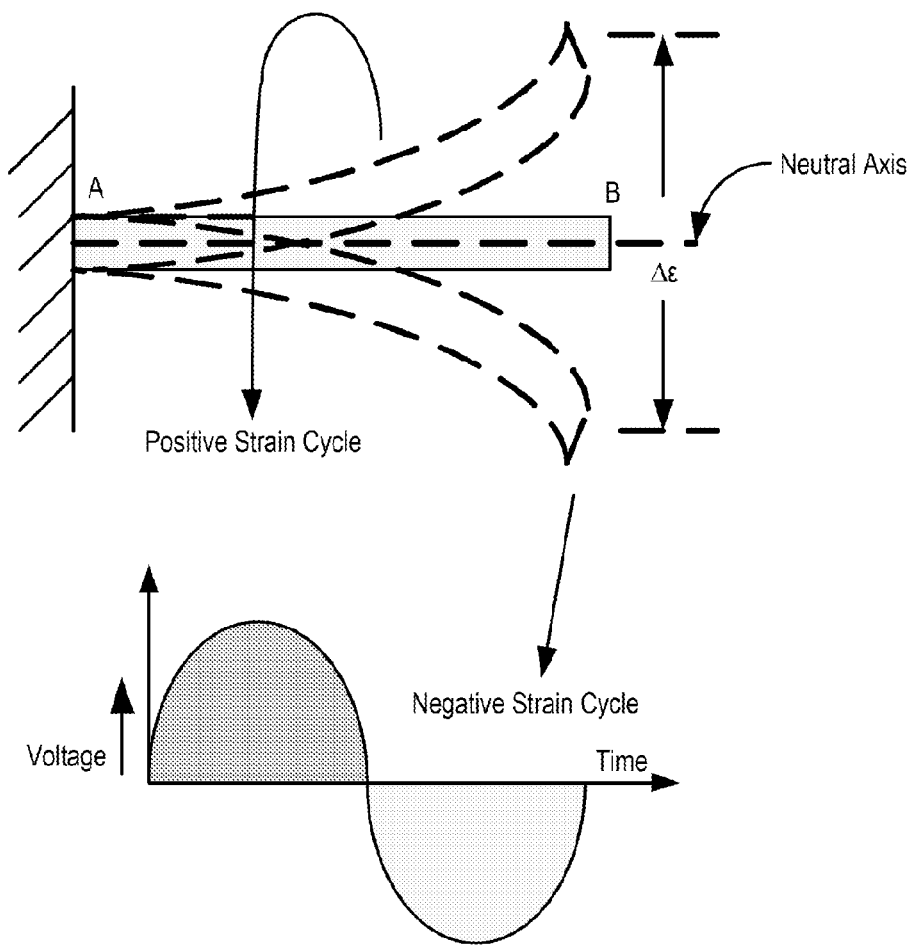
FIG. 7 is a diagram illustrating the principle underlying a self-powered static-strain sensor.

Measuring static-strain using a piezoelectric transducer poses a challenge since the device only responds to dynamic variations in strain. In another aspect of this disclosure, a self-powered static-strain sensor is presented to meet this challenge. The sensor uses a differential configuration to measure the cumulative energy during each strain-cycle. The principle is illustrated in FIG. 7 which shows the electrical signal generated by a piezoelectric cantilever beam. The positive and negative cycles of the electrical signal correspond to the deformation of the cantilever in each direction about the natural-axis or the resting state. If the cantilever returns back to its resting state (no stored potential energy), the energy transduced during the positive strain-cycle should be equal to the energy transduced during negative strain-cycle. However, if the transducer is subjected to deformation (or subjected to static-strain), there will be a difference between the positive and negative signal cycles which if integrated and measured will signify the magnitude of static-strain.

Figure 8:
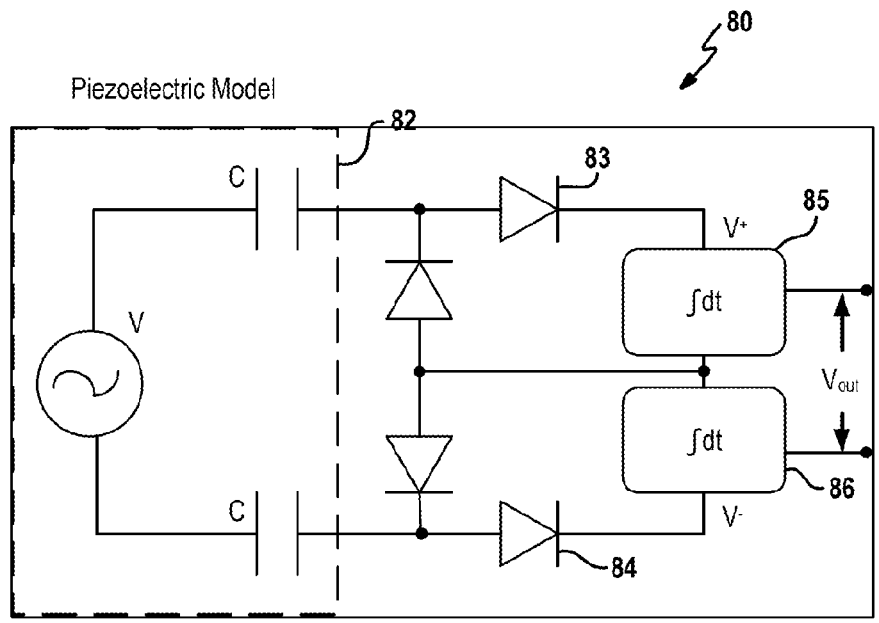
FIG. 8 is a schematic of an exemplary architecture for a self-powered static-strain sensor.

FIG. 8 depicts an exemplary architecture for the self-powered static-strain sensor 80. The sensor includes a piezoelectric transducer 82 coupled via rectifiers 83, 84 to a pair of non-volatile memory circuits 85, 86. A low-frequency model of a piezoelectric transducer is shown in FIG. 8 which consists of a strain-dependent voltage source V and a decoupling capacitor. For a piezoelectric cantilever with dimensions L×b×h and deformed according to the diagram shown in FIG. 7, the open-source voltage (V) generated across the transducer as a function of the applied mechanical force (F) is given by:

$$V = \frac{F_{g31}}{b} = SY^E h_{g31} = \frac{SY^E d_{31} h}{\epsilon} \quad (15)$$

where $g_{31}$ and $d_{31}$ are piezoelectric constants, S is the applied mechanical strain, $Y^E$ is the short circuit elastic modulus and $\epsilon$ is the electrical permittivity. The capacitance C is given by:

$$C = \frac{LB\epsilon}{h} \quad (16)$$

During the positive and negative strain-cycles (see FIG. 1) the voltages generated are given by:

$$V^+(t) = \frac{s^+(t)Y^E d_{31} h}{\epsilon} \text{ and } V^-(t) = \frac{s^-(t)Y^E d_{31} h}{\epsilon} \quad (17)$$

where $S^+(t)$ and $S^-(t)$ are the time-dependent positive and negative strain variations. The static-strain ($s_s$) can therefore be computed according to:

$$\begin{aligned} S_s &= \int (S^+(t) - S^-(t))^{dt} \\ &= \frac{\epsilon}{Y^E d_{31} h} \left[ \int V^+(t) dt - \int V^-(t)^{dt} \right] \end{aligned} \quad (18)$$

Thus, the static-strain can be computed by measuring the difference in electrical energy transduced in each of the stain-cycles.

The exemplary architecture for the self-powered static-strain sensor 80 is based on equation (18). The piezoelectric transducer 82 is configured to generate a voltage signal in response to a mechanical strain thereon. A first rectifier 83 is electrically coupled to one terminal of the piezoelectric transducer 82 and operable to extract a positive voltage $V^+$ from the voltage signal; whereas, a second rectifier 84 is electrically coupled to the other terminal of the piezoelectric transducer 82 and is operable to extract a negative voltage $V^-$ from the voltage signal. In the exemplary embodiment, the rectifiers 83, 84 are implemented by diodes although other implementations are contemplated by this disclosure. Rectified voltages are in turn used to power the pair of non-volatile memory circuits 85, 86.

In the exemplary embodiment, the non-volatile memory circuits 85, 86 are implemented using the linear hot-electron injection technique as set forth in detail above and, in particular, the memory circuit depicted in FIG. 2A. During the integration mode, the switch S is open which activates the negative feedback loop formed by the opamp A and the floating-gate transistor $M_{fg}$. The source current is held constant at $I_{ref}$ which ensures that the source-to-gate voltage $V_{sg}$ remains constant during injection. The opamp A ensures that the source-to-drain voltage $V_{sd}$ is held constant. $V_{cg}$ will linearly increase to maintain $V_{fg}$ constant. Thus, $V_{gd}$ is also held constant. So, according to equation (1) the injection current will remain constant. The programming is enabled for a fixed duration $t_2$ which ensures that a fixed amount of charge is injected onto the floating-gate. During the read-out mode, the switch $S_2$ is closed which makes $V_{cg}=0$. The floating-gate voltage $V_{fg}$ of the pMOS transistor is determined by the charge injected during the integration phase and the total capacitor $C_T$ at the floating-gate node. The change in floating gate voltage $\Delta V_{fg}$ can be calculated with the following equations:

$$\Delta V_{fg} = \frac{1}{C_T} \int I_{inj} dt = \frac{I_{inj}}{C_T} \Delta t \quad (19)$$

where $\Delta t$ is the duration of injection. As $I_{ref}$ is constant $\Delta V_{fg} = \Delta V_s$ which is read through a unity-gain buffer as shown in FIG. 3. The ratio $I_{inj}/C_T$ is the slope of the integrator which will be constant making the response linear.

The integration range of the linear p-IHEI circuit was measured experimentally. The supply voltage $V_{dd}$ was set to 6.5V, $S_2$ was enabled and $V_s$ was initialized to 4.1V (using FN-tunneling). After each integration cycle, $V_2$ was measured using an off-chip analog-to-digital converter. Since the least significant bit (LSB) voltage for differential non-linearity (DNL) is less than 0.4 mV, the equivalent resolution is above 13.4-bit.

The self-powered strain-sensor has been prototyped in a 0.5-μm standard CMOS process. A complete sensor node occupies an area of 1400 μm×1800 μm. Seven p-IHEI injectors integrated on the chip along with voltage references, read-out circuitry, two charge pumps to generate the high voltage needed for tunneling and injection, a ring oscillator and digital control circuitry.

Figure 9:
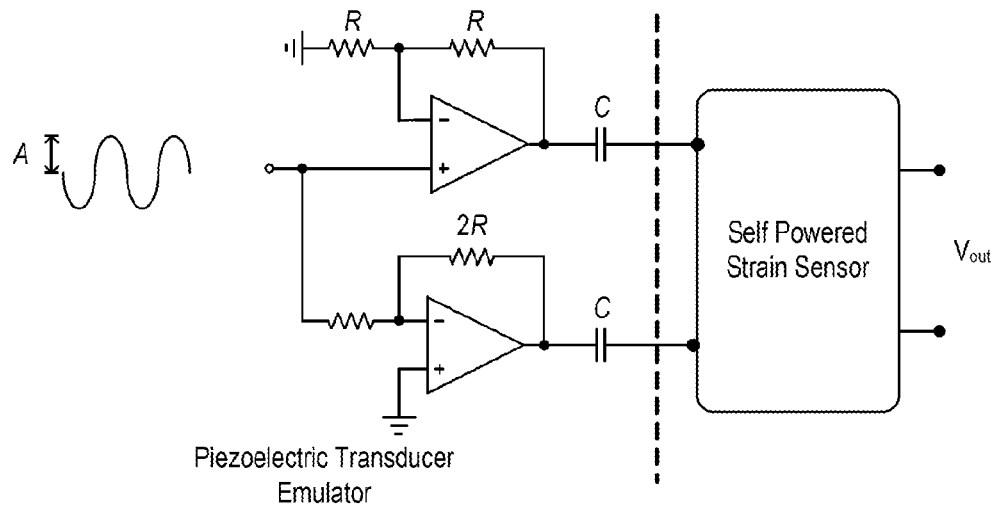
FIG. 9 is a diagram of an experimental test setup for the self-powered static-strain sensor.

The low-frequency model (see FIG. 8) of the piezoelectric transducer was emulated using two discrete COTS amplifiers shown in FIG. 9. The voltage levels and the magnitude of the decoupling capacitor was chosen according to equations (16). The output of the emulated piezo-transducer was connected to the memory circuits through the diode bridge as shown in FIG. 8.

Figure 10:
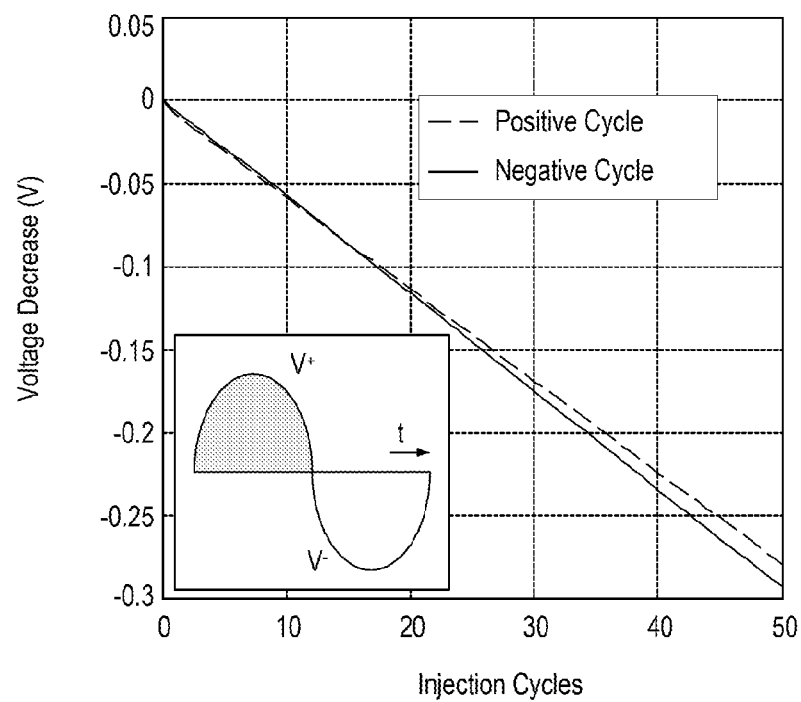
FIG. 10 is a graph illustrating sensor output with symmetrical positive and negative cycles.

In the first experiment, a signal with symmetrical positive and negative cycles was applied. Note that a minimum voltage level is required for the memory circuits to start integrating (injecting). However, this voltage level is 4.2V (for a 0.5-μm CMOS process) which can be easily generated by a piezoelectric transducer under open-load conditions. The frequency of the signal was set to 140 Hz and $S_2$ was enabled for 5 seconds, 50 times respectively for both the memory circuit. This amounted to approximately 140×5×50=3500 cycles of integration. The single ended output from each of the memory circuits is shown in FIG. 10. Note that the output voltage (proportional to the static-strain) is the difference between the two single-ended output. Even though the energy in the positive and negative cycles are equal, the differential output $\Delta V_s$, is not exactly zero, as shown in FIG. 10. This can be attributed to different injection rates due to mismatch in the opamp offset voltage in the memory circuits.

Figure 11:
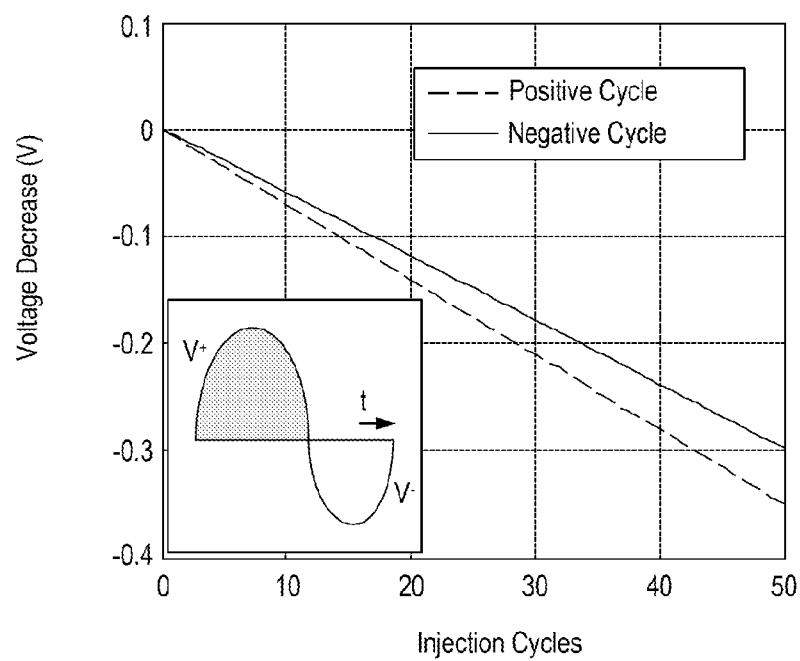
FIG. 11 is a graph illustrating sensor output with different positive and negative cycles.

In the next experiment the energy of the positive cycle was increased compared to the negative cycle as shown in FIG. 11 (insert). This time, one of the memory circuit integrates at a faster rate than the other, resulting in the increase in magnitude of the differential output voltage as shown in FIG. 11. This result validates the proof-of-concept operation of the self-powered strain-sensor.

In-vivo monitoring of mechanical strain is important in the study of osteoporosis or muscular dystrophy where the objective is to understand the progressive failure and degradation mechanisms of biomechanical structures like bones, muscles or ligaments. For example, repetitive strains greater than approximately 1500με can lead to fatigue damage and possible stress-fractures in bone. Conversely, strain-levels lower than 500με are thought to increase the risk of bone absorption and osteoporosis. The conventional and most popular method of measuring strain in-vivo is to use a passive strain-gauge (metallic or silicon-based) where the change in the electrical resistance is modulated by the change in the electrical resistance is modulated by the change in mechanical strain. Another emerging method for in-vivo strain measurement is using fiber Bragg grating (FBG) sensors which measures spectroscopic changes due to mechanical displacement of an implanted optical fiber. Even though both these techniques can precisely measure instantaneous strain-levels down to a few µε, they are passive in nature and do not provide any historical information about the strain signal which could be used for understanding progression of mechanical degradation. An example of the historical information could be some measure of the strain-energy dissipated through the biomechanical structure or could be the running average of the strain signal during the entire observation period. Without historical information, the strain-measurement could be prone to ageing artifacts of the gauge and could also be prone to the degradation in the adhesion between the gauge and the biomechanical structure being monitored. In principle, passive strain-gauges could be complemented with additional circuitry that continuously read, process and store the desired information. Continuous operation of the add-on circuitry could be achieved through powering using implanted energy storage devices (batteries or super-capacitors) that are periodically recharged either remotely or by using scavenging energy in-vivo. However, small volume requirements of the strain-gauge sensor severely limits the capacity of energy storage and in-vivo energy harvesting devices.

In the last set of experiments, the static-strain sensor 80 was interfaced with a piezoelectric transducer and was attached to a mechanical phantom that was designed to act as a biomechanical structure. The piezoelectric transducer chosen for this experiment was a commercial PZT ceramic (PZT-5H) available from Piezo Systems Inc. Note that due to lead (Pb) content, PZT transducers are generally considered bioincompatible. However, the transducer is used in this work to demonstrate the proposed proof-of-concept, even though the design could be easily translated to a polymer based piezoelectric transducer. Also, appropriate packaging and shielding ensures that PCT transducers can be used in biomechanical studies as has been reported before. Table III summarizes the mechanical and electrical specification of the PZT transducer.

TABLE III

Material Specifications of the PZT-5H Transducer

| | |
|---|---|
| Length (l) | 2.5 inch |
| Width (w) | 1.25 inch |
| Thickness (h) | .02 inch |
| Material | Lead Zirconate Titanate (PZT) |
| Electrodes | Nickel |
| Capacitance | 73 nF |
| Strain/Field ($d_{31}$) | $-190 \times 10^{-12}$ m/V |
| Field/Stress ($g_{31}$) | $-11.6 \times 10^{-3}$ V-m/N |
| coupling ($k_{31}$) | 0.35 |
| Elastic Modulus ($Y^E$) | $5.2 \times 10^{10}$ N/m$^2$ |

Figure 12:
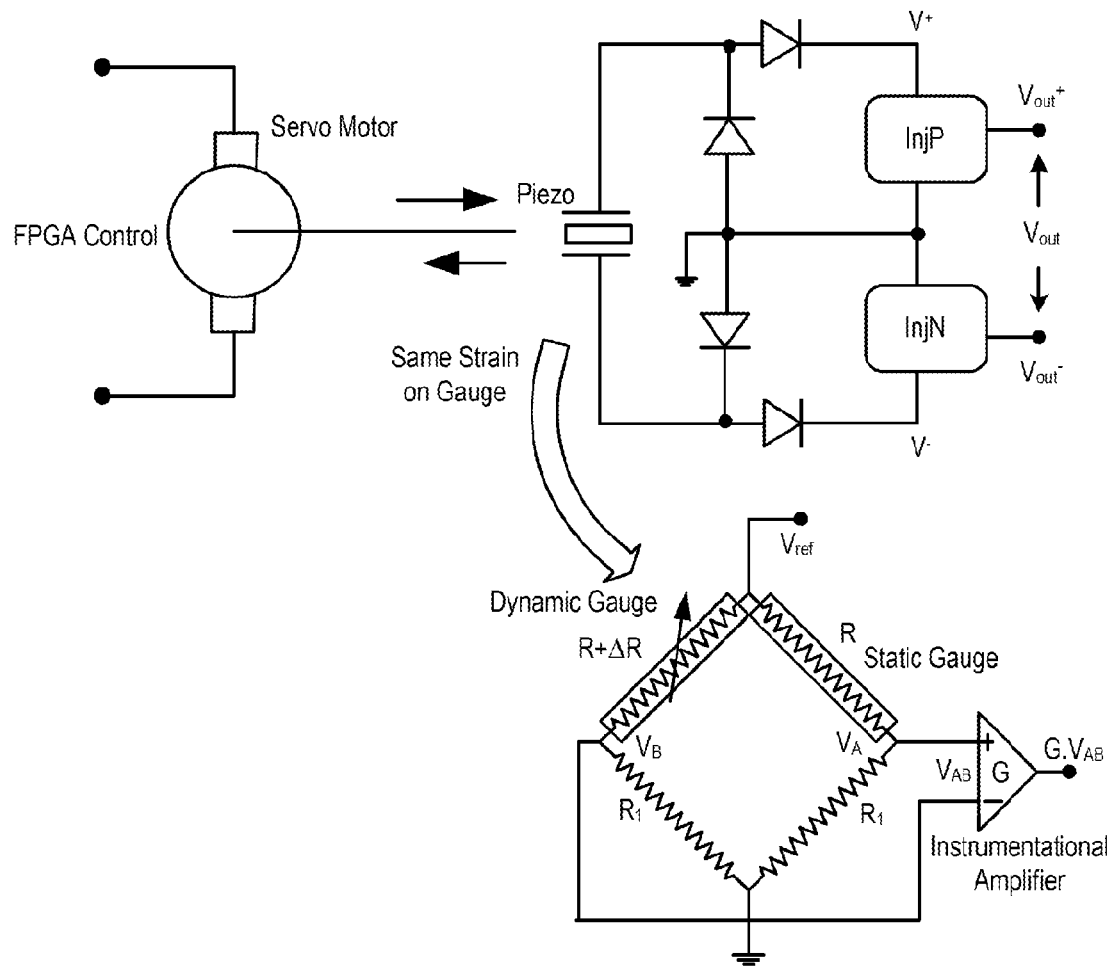
FIG. 12 is a schematic of an experimental setup of a strain-gauge attached to a plexi-glass beam.

As a biomechanical phantom, a plexi-glass beam to which the PZT transducer was attached is used as shown in FIG. 12. A programmable servo-motor was used to apply stress on the beam and the induced strain was measured/calibrated using a metallic strain-gauge as shown in the figure. The dynamics of the servo-motor was controlled using a PWM (Pulse Width Modulated) signal generated by a field-programmable gate array (FPGA). By adjusting the number of PWM cycles, the forward and backward movement of the motor shaft can be accurately controlled. The output of the PZT transducer is directly connected to the sensor IC with no additional power-sources.

The mechanical calibration of the set up was performed using a 350 Ohm(R) general purpose resistance strain-gauge. The strain-gauge was connected to a Wheatstone bridge as shown in FIG. 12 and the circuit component values are shown in Table IV. FIG. 12 also shows a calibration strain-gauge used in the Wheatstone bridge, which was used to compensate for temperature variations in strain measurements. A commercial, fully differential instrumentation amplifier was used to amplify the difference in voltages across the Wheatstone bridge.

TABLE IV

Strain-Gauge Specifications

| | |
|---|---|
| R | 350 Ω |
| $R_1$ | 1 kΩ |
| Gauge Factor (GF) | 2.11 |
| $V_{ref}$ | 5 V |

Figure 13A:
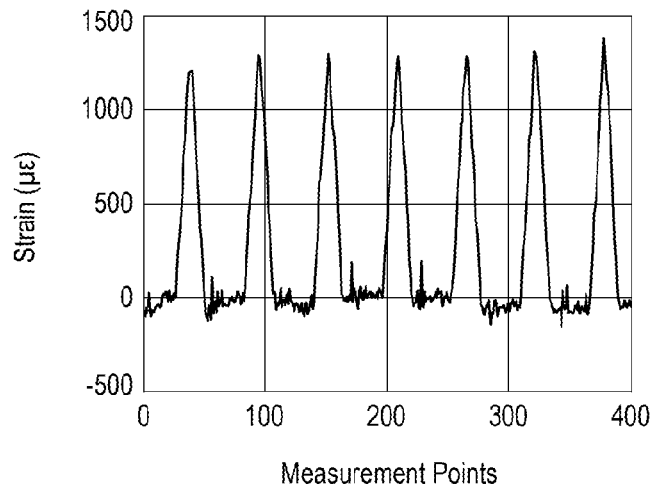
FIGS. 13A-13C are graphs illustrating time-varying strain measurements when the plexi-glass beam is periodically deformed at select maximum strain values.
Figure 13B:
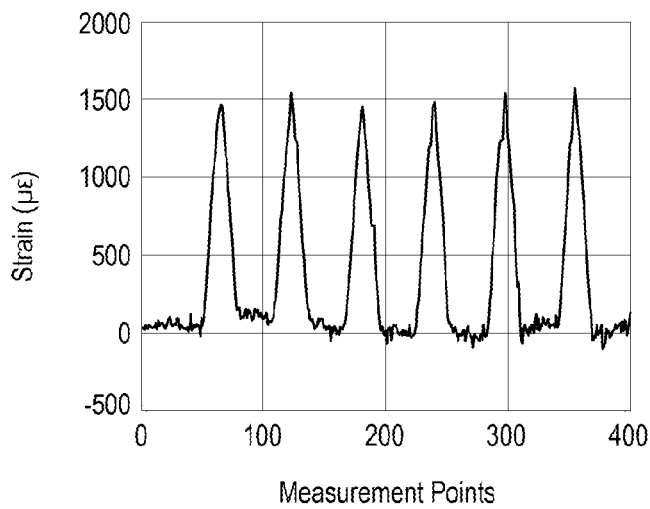
Figure 13C:
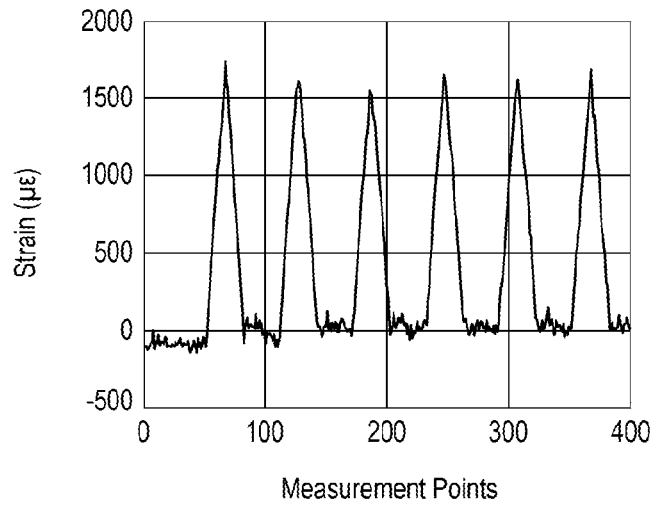
Figure 14:
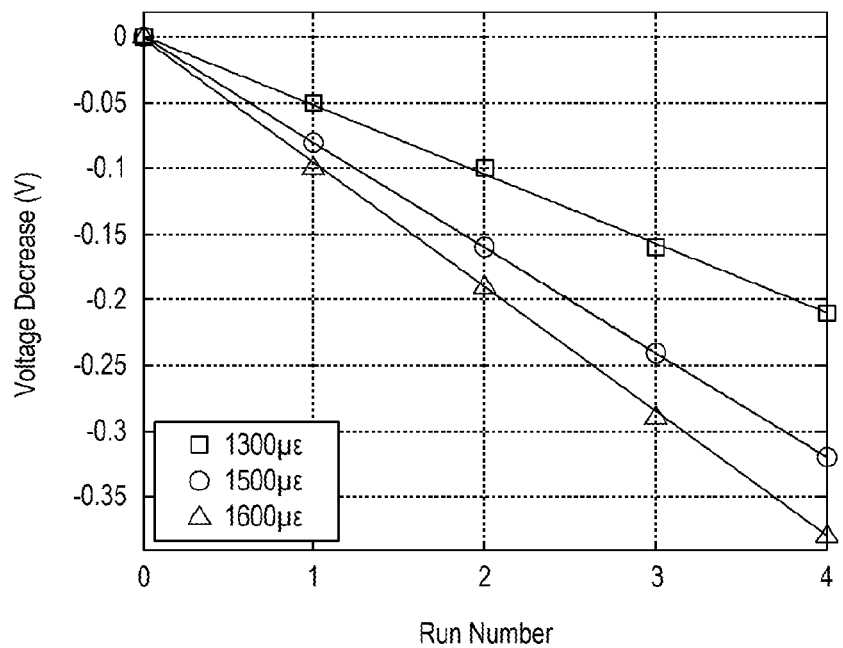
FIG. 14 is a graph illustrating measured voltage change at the output of the positive-cycle injector.
Figure 15:
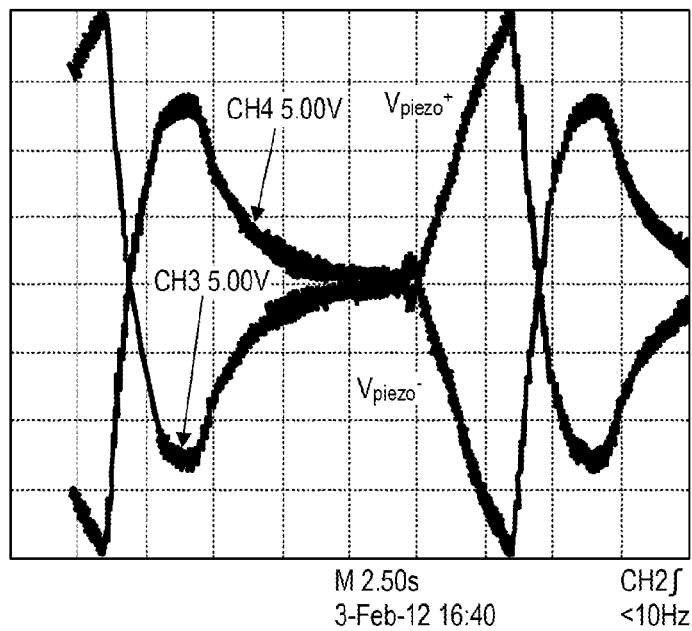
FIG. 15 is a graph illustrating output voltages of the piezoelectric transducer for a nominal strain-cycle.
Figure 16:
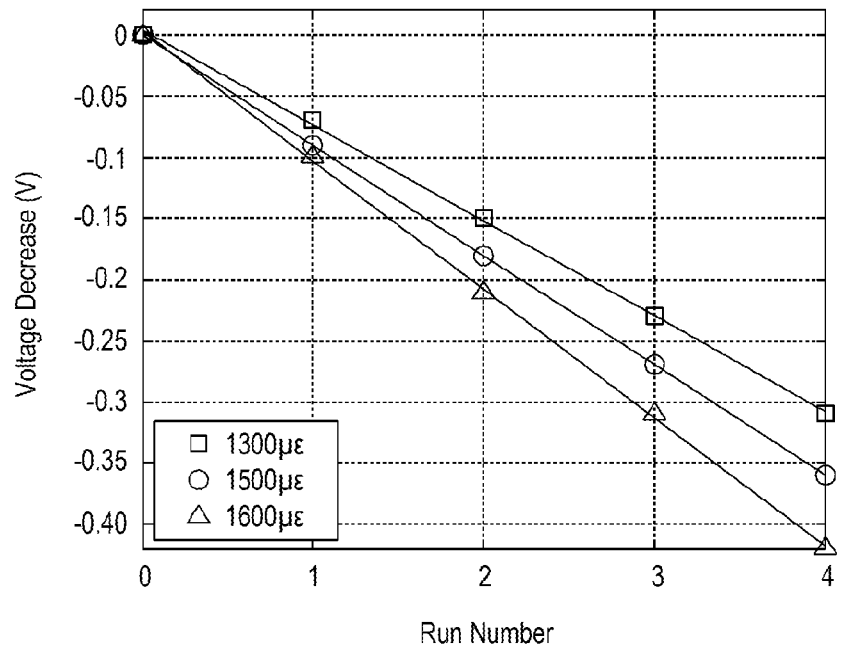
FIG. 16 is a graph illustrating measured voltage change at the output of the negative-cycle injector.

FIG. 13 shows the plots of time-varying strain (of different amplitudes) that is induced in the plexi-glass beam and FIG. 15 shows the output across the PZT transducer for one specific case. It can be clearly seen in FIG. 15 that the output voltage of the transducer shows positive and negative voltage cycles that correspond to the direction of the deformation of the beam. For all the experiments, the nominal strain-levels were chosen to be consistent with the levels experienced in biomechanical structures. The output of the sensor was measured after every 10 loading cycles and measured results are shown in FIG. 14 and FIG. 16 corresponding to both the injectors. The result shows that the response of both the injectors are similar, indicating that the energy in the positive and negative strain cycles are similar. This is expected since the plexi-glass beam is allowed to return to its resting state (zero static strain state). However, unlike conventional strain-gauges, the self-powered gauge provides a historical indicator of the $L_1$ norm that is proportional to the energy dissipated through the PZT and hence the plexi-glass beam. The energy is proportional to the average of the output generated by both the injectors. This historical information could be more useful for determining progression of damage in a structure than just a passive static-strain measurement.

Figure 17A:
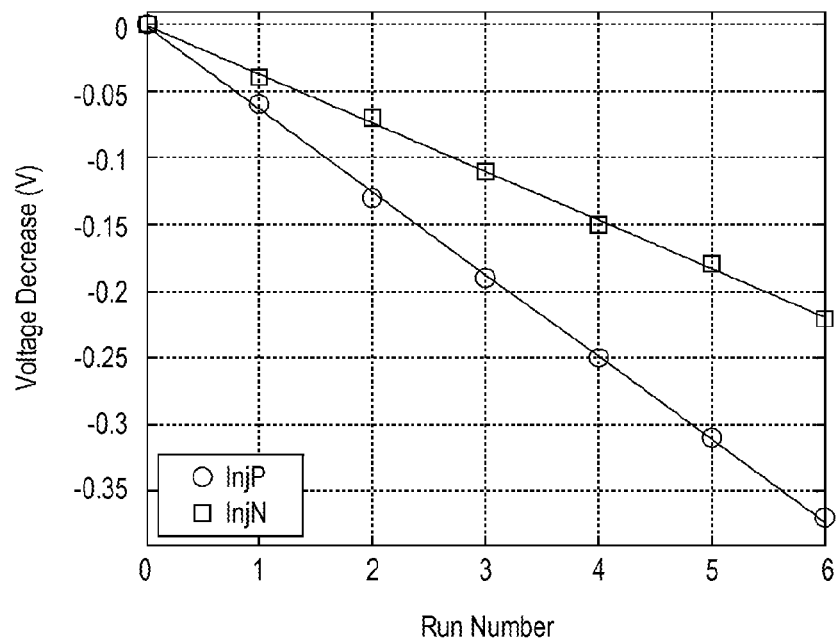
FIGS. 17A and 17B are graphs illustrating difference in measure voltage change between positive-cycle and negative-cycle injectors under different conditions.
Figure 17B:
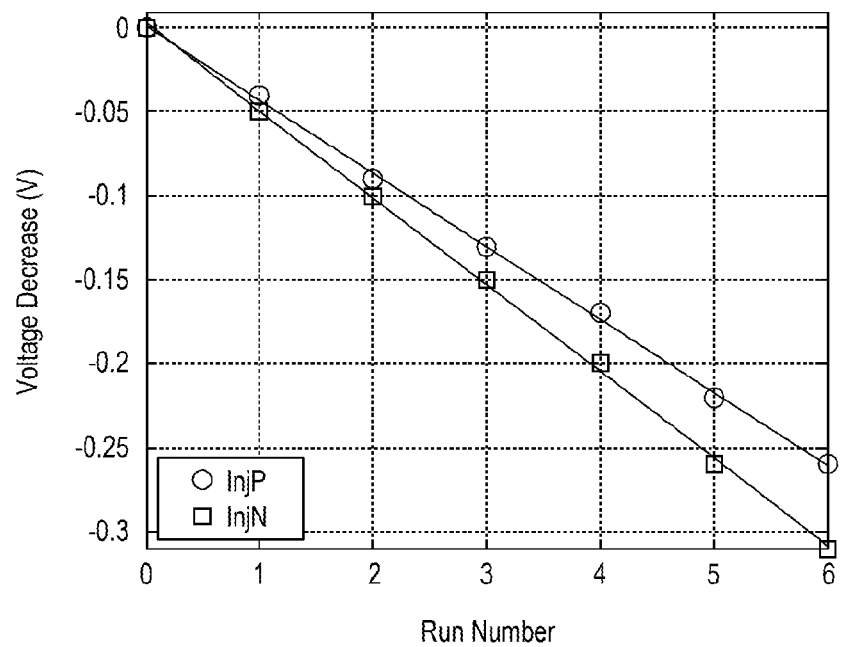

To demonstrate that the proposed sensor IC can indeed measure quasi-static strain using a real piezoelectric transducer, the following experiment was designed. The servo-motor was programmed to generate strain-levels according to the waveform. The waveform shows that the plexi-glass beam is not allowed to return to its resting-state, implying that the measured strain at the start of the experimental run is not equal to the measured strain at the end of the experimental run. After each run, the output of the injectors are measured before the beam is subjected to a similar strain-cycle. FIG. 17A shows difference between the output of the injectors decreases with each run, which is proportional to the level of the quasi-static strain. Also the first injector measures a larger decrease in the output voltage as compared to the second injector. When the same experiment is repeated however, after swapping the input terminals of the sensor, the second injector measures a larger decrease in the output voltage (after calibrating for mismatch effects) as shown in FIG. 17B, which is consistent with the expected results.

In this disclosure, a self-powered static-strain sensor is provided using a differential configuration of a linear p-IHEI (piezo-IHEI) circuit. The sensor is powered directly from ambient strain-variations and therefore does not require any batteries. For this reason, the proposed sensor could be miniaturized and used in in-vivo and embedded monitoring application. However, the sensor requires a minimum voltage-level (or strain-level) for operation which introduces dead-zones in its response which is unlike traditional strain-gauges that can be used to measure ultra-low levels of strain. Also, the current version of the self-powered sensor suffers from mismatch due to its analog components (rectifiers, references and floating-gate injectors) and is sensitive to temperature variations. Compensation of mismatch therefore requires post-measurement calibration. The mismatch (in injection rates) between the injectors is first estimated (using controlled mechanical excitation) and is then used for calibration.

Another important aspect is the scalability of the concept and design to deep-sub-micron and nanoscale (CMOS) processes. In this regard, note that hot-electrons require a minimum of 3.2 eV to surmount the silicone-di-oxide barrier (difference in conduction band levels) and unfortunately this value does not scale with technology. For this reason, high-voltage charge-pumps would still be required at least for interrogation and programming. However, in sub-100 nm processes quantum mechanical tunneling through gate-oxide could be used instead of the hot-electron injection process. But it remains to be verified how the physics of tunneling could be exploited to obtain the functionality of the strain-gauge. Also, gate-leakage could also pose a significant data retention problem for the processes with smaller feature size.

Another important consideration is the long-term reliability of the self-powered strain-gauge. Most high-voltage failure mechanisms in a CMOS process are attributed to: (a) avalanche breakdown and (b) oxide breakdown. In avalanche breakdown, the impact ionization leads to a positive feedback process that culminates with the failure of the transistor. In this work, the avalanche process is carefully controlled by starving the source current of the transistor. As a result, the injector is a negative feedback circuit where the number of electrons injected into the oxide is significantly limited. In fact the injector has operated continuously for days without observing any failure. The second failure mechanism is due to the oxide breakdown where repeated application of high electric field creates traps finally lead to its breakdown. For the 0.5-μm CMOS process voltages greater than 15 V are required for quantum mechanical tunneling and for creating stress related artifacts. As described earlier FN-tunneling is only used for initialization and reprogramming of the sensor which is performed very infrequently.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A self-powered static-strain sensor, comprising:
a piezoelectric member that generates a voltage in response to as mechanical strain; and
a non-volatile memory circuit powered by the voltage received from the piezoelectric member and includes
a floating gate transistor having a gate node and a source node;
a capacitor having a first terminal and a second terminal, the first terminal electrically coupled to the gate node of the floating gate transistor;
a current reference circuit electrically coupled to the source node of the floating gate transistor and operable to source a current therein; and
a feedback circuit electrically coupled between the source node of the floating gate transistor and the second terminal of the capacitor, and operable to adjust a voltage at the gate node of the floating gate transistor in accordance with a source-to-drain voltage across the floating gate transistor.

2. The self-powered static-strain sensor of claim 1 wherein the current reference circuit operates to hold the source current constant, thereby ensuring that the source-to-gate voltage of the floating gate transistor remains constant.

3. The self-powered static-strain sensor of claim 1 wherein the current reference circuit is implemented by two transistors in a cascading arrangement.

4. The self-powered static-strain sensor of claim 1 wherein the feedback circuit is further defined as an operational amplifier having an inverting terminal electrically coupled to the source node of the floating gate transistor, a non-inverting terminal electrically coupled to a reference voltage and an output electrically coupled to the second terminal of the capacitor.

5. The self-powered static-strain sensor of claim 1 wherein the feedback circuit is further defined as a single-stage, single ended amplifier.

6. The self-powered static-strain sensor of claim 1 wherein the non-volatile memory circuit further comprises a tunnel capacitor electrically coupled to the gate node of the floating gate transistor for removing electrons from the floating gate transistor.

7. The self-powered static-strain sensor of claim 1 wherein the non-volatile memory circuit further comprises:
a switch electrically coupled between the second terminal of the capacitor and ground; and
a controller interfaced with the switch to control operation thereof, such that the switch is opened to inject current into the floating gate transistor and is closed to remove electrons from the floating gate transistor.

8. The self-powered static-strain sensor of claim 1 further comprises a rectifier interposed between the piezoelectric member and the non-volatile memory circuit.

9. A self-powered static-strain sensor, comprising:
a piezoelectric member that generates a voltage in response to as mechanical strain;
a non-volatile memory arrangement having an array of memory circuits powered by voltage received from the piezoelectric member, each memory circuit includes
a floating gate transistor having a gate node and a source node;
a capacitor having a first terminal and a second terminal, the first terminal electrically coupled to the gate node of the floating gate transistor;
a current reference circuit electrically coupled to the source node of the floating gate transistor and operable to source a current therein;
a feedback circuit electrically coupled between the source node of the floating gate transistor and the second terminal of the capacitor, and operable to adjust a voltage at the gate node of the floating gate transistor in accordance with a source-to-drain voltage across the floating gate transistor; and
a switch electrically coupled between the second terminal of the capacitor and ground; and
a controller interfaced with each of the switches in the array of memory circuits to control operation thereof.

10. The self-powered static-strain sensor of claim 9 wherein the current reference circuit in each memory circuit operates to hold the source current constant, thereby ensuring that source-to-gate voltage of the corresponding floating gate transistor remains constant.

11. The self-powered static-strain sensor of claim 9 wherein the current reference circuit is implemented by two transistors in a cascading arrangement.

12. The self-powered static-strain sensor of claim 9 wherein the feedback circuit is further defined as an operational amplifier having an inverting terminal electrically coupled to the source node of the floating gate transistor, a non-inverting terminal electrically coupled to a reference voltage and an output electrically coupled to the second terminal of the capacitor.

13. The self-powered static-strain sensor of claim 9 wherein each memory circuit further comprises a tunnel capacitor electrically coupled to the gate node of the floating gate transistor for removing electrons from the floating gate transistor.

14. A self-powered static-strain sensor, comprising:
a piezoelectric member having a first and second terminal and operable to generate a voltage signal in response to a mechanical strain;
a first rectifier electrically coupled to the first terminal of the piezoelectric member and operable to extract a positive voltage from the voltage signal;
a first non-volatile memory circuit powered by the positive voltage received from the first rectifier, the first non-volatile memory includes
a first floating gate transistor having a gate node and a source node;
a first capacitor having a first terminal and a second terminal, the first terminal electrically coupled to the gate node of the first floating gate transistor;
a first current source electrically coupled to the source node of the first floating gate transistor and operable to source an injection current into the first floating gate transistor; and
a first feedback circuit electrically coupled between the source node of the first floating gate transistor and the second terminal of the first capacitor, and operable to adjust a voltage at the gate node of the floating gate transistor in accordance with a source-to-drain voltage across the first floating gate transistor;
a second rectifier electrically coupled to the second terminal of the piezoelectric member and operable to extract a negative voltage from the voltage signal;
a second non-volatile memory circuit powered by the negative voltage received from the second rectifier, the second non-volatile memory includes
a second floating gate transistor having a gate node and a source node;
a second capacitor having a first terminal and a second terminal, the first terminal electrically coupled to the gate node of the second floating gate transistor;
a second current source electrically coupled to the source node of the second floating gate transistor and operable to source an injection current into the second floating gate transistor; and
a second feedback circuit electrically coupled between the source node of the second floating gate transistor and the second terminal of the first capacitor, and operable to adjust a voltage at the gate node of the second floating gate transistor in accordance with a source-to-drain voltage across the second floating gate transistor.

15. The self-powered static-strain sensor of claim 14 wherein the first current source is configured to receive the positive voltage and generate the injection current for the first floating gate transistor, and the second current source is configured to receive the negative voltage and generate the injection current for the second floating gate transistor.

16. The self-powered static-strain sensor of claim 14 wherein the first and second feedback circuits are further defined as an operational amplifier having an inverting terminal electrically coupled to the source node of the respective floating gate transistor, a non-inverting terminal electrically coupled to a reference voltage and an output electrically coupled to the second terminal of the capacitor.

17. The self-powered static-strain sensor of claim 14 wherein the first and second non-volatile memory circuits further include a tunnel capacitor electrically coupled to the gate node of the respective floating gate transistor for removing electrons from the floating gate transistor.

18. The self-powered static-strain sensor of claim 17 wherein the first and second non-volatile memory circuits further include a switch electrically coupled between the second terminal of the capacitor and ground, such that the switch is closed to remove electrons from the respective floating gate transistor.

* * * * *